United States Patent [19]

Ohta

[11] Patent Number: 4,755,514
[45] Date of Patent: Jul. 5, 1988

[54] PHENYLPYRAZINE DERIVATIVES AND THROMBOLYTIC AGENT

[75] Inventor: Akihiro Ohta, Tokyo, Japan

[73] Assignee: Suntory Limited, Osaka, Japan

[21] Appl. No.: 861,314

[22] Filed: May 9, 1986

[30] Foreign Application Priority Data

May 10, 1985 [JP] Japan .................................. 60-99382

[51] Int. Cl.$^4$ .................. A61K 31/495; G07B 241/12
[52] U.S. Cl. ..................................... 514/255; 544/336; 544/410
[58] Field of Search ................. 544/336, 410; 514/255

[56] References Cited

FOREIGN PATENT DOCUMENTS 58-043961  3/1983  Japan ................................... 544/336

OTHER PUBLICATIONS

Duenger, et al., Chem. Abstracts, vol. 73 (1970), entry 106474e.
Soldatenkov, et al, Chem. Abstracts, vol. 99 (1983), entry 175563g.
Tada, et al, Chem. Abstracts, vol. 94 (1981), entry 46467b.
Soldatenkov, A. T., Bagdadi, M. V., Radzhan, P. K., Brindkha, O. S., Edogiaverie, S. L., Fomichev, A. A. and Prostakov, N. S., Plenum Publishing Corporation, (Translated from Zhurnal Organicheskoi Khimii, vol. 19, No. 6, pp. 1326–1332, Jun. 1983).
Dünger South African Patent Appln 69-6582 dtd Sep. 1, 1969.
Chemistry Letters, Aug. 1980, pages 921–924.
The Chemical Society of Japan, M. Tada et al.

Primary Examiner—Robert Gerstl
Assistant Examiner—William A. Teoli, Jr.
Attorney, Agent, or Firm—Cushman, Darby & Cushman

[57] ABSTRACT

Novel phenylpyrazine derivatives of the following general formula:

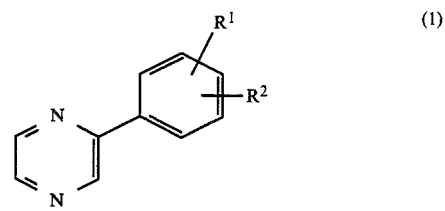

(where $R^1$ is a hydrogen atom, a halogen atom, a lower alkyl group, a lower alkoxy group or a hydroxyl group; and $R^2$ is a halogen atom, a lower alkyl group, a lower alkoxy group or a hydroxyl group) have a high degree of thrombolytic activity in comparison with a known thrombolytic agent, Ticlopidine. Moreover, their toxicities are very low. Therefore, the derivatives are extremely useful as thrombolytic agents.

6 Claims, No Drawings

PHENYLPYRAZINE DERIVATIVES AND THROMBOLYTIC AGENT

The present invention relates to a novel phenylpyrazine derivative having the general formula:

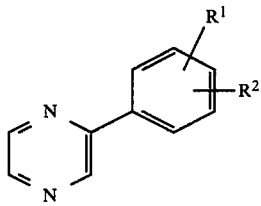

(where $R^1$ is a hydrogen atom, a halogen atom, a lower alkyl group, a lower alkoxy group or a hydroxyl group; and $R^2$ is a halogen atom, a lower alkyl group, a lower alkoxy group or a hydroxyl group), and a thrombolytic composition comprising said derivative as the active ingredient.

With the recent westernization of eating habits, the extension of the average lifetime and the increase in the aged population in Japan, the number of patients suffering from thrombotic diseases is increasing and there is a growing need to provide management for the prevention and treatment of these diseases. The thrombolytic agents used today in the treatment of thromboembolic diseases are roughly divided into two groups, depending on the mechanism of their action: those of the first group are fibrinolytic factors which directly enhance the fibrinolytic activity in blood, urokinase is a representative example. Thrombolytic agents of the first group must be used with the utmost care since they may cause hemorrhagic emboli if administered in large dose. Thrombolytic agents of the second group exhibit no detectable fibrinolytic action by themselves, but will produce enhanced fibrinolysis when administered in vivo. While a number of drugs are known to belong to the second group, there is a strong need to develop compounds which produce fewer side effects and are less toxic.

Drugs of the second group are often administered to patients during their recuperation in order to prevent the recurrence of thrombosis, or to normal persons for the purpose of preventing thrombosis. Since these drugs must be administered perorally for a prolonged period, it is essential that they made safer and present a lower toxicity. Therefore, the principal object of the present invention is to provide a thrombolytic agent that has a lower degree of toxicity and that can be administered perorally for a prolonged period without causing any danger to the patient.

In accordance with one aspect, the present invention provides a phenylpyrazine derivative of the following general formula (1) which is a novel compound and has a thrombolytic action. In accordance with another aspect, the present invention provides a thrombolytic agent containing the above derivative as the active ingredient thereof.

The compound of the present invention having the general formula:

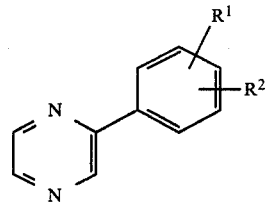

(where $R^1$ is a hydrogen atom, a halogen atom, a lower alkyl group, a lower alkoxy group or a hydroxyl group; and $R^2$ is a halogen atom, a lower alkyl group, a lower alkoxy group or a hydroxyl group) may be produced by reacting ethylenediamine or a salt thereof with a glyoxal derivative of the general formula:

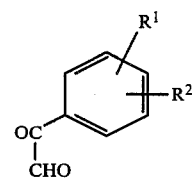

(where $R^1$ and $R^2$ have the same meanings as defined above).

This process starts with the mixing of ethylenediamine or a salt thereof with a glyoxal derivative at room temperature or below. Best results are obtained if alcohols are used as solvents but, alternatively, ethers such as dioxane may be employed.

In the second step, the reaction mixture is heated after the addition of a base. Preferable examples of the base are sodium hydroxide, potassium hydroxide and lithium hydroxide. The heating temperature is preferably within the range of 50° to 150° C. It will be obvious to those skilled in the art that the compound of Formula (1) may be obtained in exactly the same manner even if ethylenediamine is replaced by a salt thereof.

After the completion of the reaction, water is added to the reaction mixture and the crude product, after being extracted with a water-immiscible organic solvent, is purified by a suitable technique such as column chromatography, preparative thin-layer chromatography, distillation or recrystallization. These procedures ensure that the compound of the present invention is obtained in a pure form.

As will be apparent from the results of the pharmacological tests conducted in Example 9, given later in this specification, the compounds of the present invention have superior thrombus-preventing effects.

The phenylpyrazine derivative of the present invention may be used for the purpose of preventing the occurrence of various thrombotic diseases. The dosage of the active compound of the present invention will, of course, depend on the route of administration, the severity of the disease and the general condition of the patient. A desirable dosage is within the range of 50 to 2000 mg per day for an adult, with an optimum dosage lying within the range of 200 to 1000 mg per day for an adult. The compounds of Formula (1) are believed to have no toxicity since they could be administered perorally to mice at a dosage of 5 g/kg without causing any apparent change in the general condition of the animals.

The compounds of the present invention are best administered perorally, but they may be administered by injection or topical application.

The compounds of the present invention may be worked into dosage forms such as tablets, powders, granules, capsules, injections or suppositories, either independently or after being mixed with pharmaceutically-acceptable carriers or excipients by standard methods. Typical examples of such pharmaceutical carriers or excipients include glucose, potassium phosphate, calcium carbonate, starch, sucrose, lactose, carboxymethyl cellulose calcium, talc, and magnesium stearate. The compounds may be stabilized by encapsulation with cyclodextrin or other shell-forming materials.

In addition to the solid dosage forms, the compounds of the present invention may be worked into liquids such as oily suspensions or syrups. If the disease occurs at sites where the drug can be administered transdermally, the compounds may be worked into ointments or pastes which are effective for the purpose of treating the disease at such sites.

EXAMPLES

The following examples are provided in order to further illustrate the present invention, but are in no sense to be taken to limit the scope of the invention.

EXAMPLE 1

2-(4-chlorophenyl)pyrazine

Ethylenediamine (1.96 g, 31.6 mmol) was dissolved in ethanol (50 ml). To the stirred solution, 4.9 g (26.3 mmol) of 4′-chlorophenylglyoxal monohydrate was added in small portions at temperatures not of higher than room temperature. The mixture was stirred for an additional 30 minutes at room temperature. Thereafter, 1.60 g of potassium hydroxide was added, and the resultant mixture was refluxed for 5 hours. After the completion of the reaction, excess reagents and solvent were distilled off under vacuum, and the mixture of the residue with water was subjected to extraction with chloroform. The organic layer was concentrated and subjected to column chromatography in a Wakogel C-200. Upon elution with benzene, 2.57 g of the titled compound was obtained (yield, 51%).

Nature: colorless needles (in hexane).
Melting point: 77°–77.5° C.
Mass spectrum (m/z): 190 (M+).
$^1$H-NMR spectrum (CDCl$_3$, δ ppm): 7.33(2H, d, J=8 Hz), 7.83(2H, d, J=8 Hz), 8.37(1H, d, J=3 Hz), 8.48(1H, dd, J=2, 3 Hz), 8.87(1H, d, J=2 Hz).
Elemental analysis (for C$_{10}$H$_7$ClN$_2$): Cal'd (%): C 63.00, H 3.70, N 14.70. Found (%): C 62.95, H 3.66, N 14.75.
UV spectrum (95% ethanol, nm, log ε): 252 (4.14), 285 (4.14).

EXAMPLE 2

2-(4-methylphenyl)pyrazine

The procedure of Example 1 was repeated, using 16 g (0.267 mol) of ethylenediamine, 32.0 g (0.216 mol) of 4-methylphenylglyoxal, 450 ml of ethanol and 13.2 g of potassium hydroxide, with the result that 11.0 g of the titled compound was obtained (yield: 30%).

Nature: colorless needles (in hexane).
Melting point: 54°–55° C.
Mass spectrum (m/z): 170 (M+).
$^1$H-NMR spectrum (CDCl$_3$, δ ppm): 2.30(3H, s), 7.17(2H, d, J=8 Hz), 7.73(2H, d, J=8 Hz), 8.30(1H, d, J=3 Hz), 8.43(1H, dd, J=2, 3 Hz), 8.87(1H, d, J=2 Hz).
Elemental analysis (for C$_{11}$H$_{10}$N$_2$): Cal'd (%): C 77.62, H 5.92, N 16.46. Found (%): C 77.75, H 5.89, N 16.47.
UV spectrum (95% ethanol, nm, log ε): 254 (3.76), 288 (3.70).

EXAMPLE 3

2-(4-methoxyphenyl)pyrazine

The procedure of Example 1 was repeated, using 10.68 g (0.178 mol) of ethylenediamine, 27.0 g (0.148 mol) of 4-methylphenylglyoxal monohydrate, 200 ml of ethanol and 9.01 g of potassium hydroxide. 10.1 g of the titled compound was produced (yield: 37%).

Nature: colorless needles (in hexane).
Melting point: 86°–87° C.
Mass spectrum (m/z): 186 (M+).
$^1$H-NMR spectrum (CDCl$_3$, δ ppm): 3.83(3H, s), 7.00(2H, d, J=10 Hz), 7.97(2H, d, J=10 Hz), 8.43(1H, d, J=3 Hz), 8.57(1H, dd, J=2, 3 Hz), 9.00(1H, d, J=2 Hz).
Elemental analysis (for C$_{11}$H$_{10}$N$_2$O): Cal'd (%): C 70.95, H 5.41, N 15.04. Found: (%): C 71.24, H 5.46, N 15.12.
UV spectrum (95% ethanol, nm, log ε): 210 (4.02), 238 (3.93), 267 (4.05), 290 (4.07), 321 (4.00).

EXAMPLE 4

2-(3-chlorophenyl)pyrazine

The procedure of Example 1 was repeated, except that the 4-chlorophenylglyoxal monohydrate was replaced by 3-chlorophenylglyoxal. The titled compound was obtained at a yield of 90%.

Nature: colorless needles (in hexane).
Melting point: 53°–54° C.
Mass spectrum (m/z): 190 (M$^{30}$).
$^1$H-NMR spectrum (CDCl$_3$, δ ppm): 7.33(2H, m), 7.67–7.93(2H, m), 8.43(1H, d, J=3 Hz), 8.50(1H, dd, J=2, 3 Hz), 8.90(1H, d, J=2 Hz).
Elemental analysis (for C$_{10}$H$_7$ClN$_2$): Cal'd (%): C 63.00, H 3.70, N 14.70. Found (%): C 63.20, H 3.52, N 14.54.
UV spectrum (95% ethanol, nm, log ε): 215 (4.25), 243 (4.07), 285 (4.06).

EXAMPLE 5

2-(2,4-dichlorophenyl)pyrazine

The procedure cf Example 1 was repeated, except that the 4-chlorophenylglyoxal monohydrate was replaced by 2,4-chlorophenylglyoxal. The titled compound was obtained at a yield of 90%.

Nature: colorless needles (in methanol).
Melting point: 131°–132° C.
Mass spectrum (m/z): 224 (M+).
$^1$H-NMR spectrum (CDCl$_3$, δ ppm): 7.20–7.60(3H, m), 8.50(1H, d, J=Hz), 8.60(1H, dd, J=2, 3 Hz), 8.90(1H, d, J=2 Hz).
Elemental analysis (for C$_{10}$H$_6$Cl$_2$H$_2$): Cal'd (%): C 53.36, H 2.69, N 12.45. Found (%): C 53.50, H 2,84, N 12.19.
UV spectrum (95% ethanol, nm, log ε): 2.14 (4.23), 245 (3.88), 278 (4.02).

EXAMPLE 6

2-(3,4-dichlorophenyl)pyrazine

The procedure of Example 1 was repeated, except that the 4-chlorophenylglyoxal monohydrate was replaced by 3′,4′-chlorophenylglyoxal. The titled compound was obtained at a yield of 91%.

Nature: colorless needles (in methanol).
Melting point: 122°–124° C.
Mass spectrum (m/z): 224 (M+).
$^1$H-NMR spectrum (CDCl$_3$, δ ppm): 7.47(1H, d, J=8 Hz), 7.77(1H, dd, J=2, 8 Hz), 8.08(1H, d, J=3 Hz), 8.47(1H, d, J=3 Hz), 8.50(1H, dd, J=2, 3 Hz), 8.92(1H, d, J=2 Hz).
Elemental analysis (for C$_{10}$H$_6$Cl$_2$N$_2$): Calc'd (%): C 53.36, H 2.69, N 12.45. Found (%): C 53.50, H 2.69, N 12.43.
UV spectrum (95% ethanol, nm, log ε): 215 (4.27), 252 (4.07), 286 (4.11).

EXAMPLE 7

2-(2-chlorophenyl)pyrazine

The procedure of Example 1 was repeated, using 1.96 g (3.16 mmol) of ethylenediamine, 4.9 g (2.13 mmol) of 2-chlorophenylglyoxal monohydrate, 1.6 g of potassium hydroxide and 50 ml of ethanol, with the result that 2.0 g of the titled compound was obtained (yield: 49%).

Melting point: 38°–39° C.
Boiling point: 115° C./2 mmHg
Mass spectrum (m/z): 190 (M+).
$^1$H-NMR spectrum (CDCl$_3$, δ ppm): 7.40(4H, m), 8.55(1H, d, J=3 Hz), 8.67(1H, dd, J=2, 3 Hz), 8.97(1H, d, J=2 Hz).
Elemental analysis (for C$_{10}$H$_7$ClN$_2$): Cal'd (%): C 63.00, H 3.70, N 14.70. Found (%): C 63.23, H 3.77, N 14.52.
UV spectrum (95% ethanol, nm, log ε): 213 (4.20), 276 (3.96).

EXAMPLE 8

2-(4-hydroxyphenyl)pyrazine

The procedure of Example 1 was repeated, except that the 4-chlorophenylglyoxal monohydrate was replaced by 4-hydroxyphenylglyoxal. The titled compound was obtained at a yield of 23%.

Nature: pale yellow prisms (in methanol).
Melting point: 216°–217° C.
Mass spectrum (m/z): 172 (M+).
$^1$H-NMR spectrum (CD$_3$OD, δ ppm: 4.90(1H, s), 6.87(2H, d, J=8 Hz), 7.90(2H, d, J=8 Hz), 8.37(1H, d, J=3 Hz), 8.57(1H, q, J=2 and 3 Hz), 8.97(1H, d, J=2 Hz).
Elemental analysis (for C$_{10}$H$_8$N$_2$O): Cal'd (%): C 69.75, H 4.68, N 16.27. Found (%): C 69.71, H 4.72, N 16.11.
UV spectrum (95% ethanol, nm, log ε): 2.39 (4.06), 269 (4.21), 290 (4.25), 324 (4.15).

EXAMPLE 9

Pharmacological tests

The following tests were conducted to evaluate the effect of the claimed compounds in the prevention of pulmonary embolic death in mice.

Compound tested

Each of the compounds being tested was suspended in 0.5% carboxymethyl cellulose and administered perorally at a dosage of 300 mg/kg (0.1 ml/10 g body weight).

Experimental animals

Male ddY mice weighing 18–20 g were subjected to the test after being starved overnight.

Method

Three hours after oral administration of a selected test compound to the mice, 30 mg/kg of adenosine-5′-diphosphate sodium salt (Sigma Chemical Co., Grade IX) or collagen was injected through their tail veins. The number of mice which died of pulmonary embolism within 3 minutes after the intravenous injections was counted.

The adenosine-5′-diphosphate sodium salt (ADP 2Na) was in the form of a solution in physiological saline at a concentration of 300 mg/10 ml. The collagen was administered in the form of a solution which was prepared by the following procedure: 25 mg of collagen was uniformly sonicated in a solution containing 25 mmol of tris-HCl and 130 mmol of sodium chloride (pH: 7.3), and the resultant dispersion was incubated at 37° C. for 45 minutes to form a polymer (after incubation, the collagen solution was kept in ice-water until it was used).

As a control, 0.5% carboxymethyl cellulose (10 ml/kg) was administered through tail veins.

Results

In the control group, all the animals which were tested died as a result of the administration of ADP 2Na or collagen. The test results are summarized in Table 1.

TABLE 1

| Compound name (Example No.) | Dosage (mg/kg) | Number of animals dying within 3 minutes after injection/ Number of animals in test | |
|---|---|---|---|
| | | ADP 2Na | Collagen |
| 1 | 300 | 4/9 | 2/8 |
| 2 | 300 | 3/7 | 7/8 |
| 3 | 300 | 4/7 | 6/8 |
| 4 | 300 | 5/10 | 6/10 |
| 5 | 300 | 6/10 | 4/10 |
| 6 | 300 | 3/10 | 4/10 |
| 7 | 300 | 5/10 | 6/9 |
| 8 | 300 | 4/7 | 7/8 |
| Control | — | 6/6 | 6/6 |

As the table shows, the compounds prepared in Examples 1 and 6 exhibited thrombolytic effects which were equal to or greater than the levels achieved by a known thrombolytic agent, Ticlopidine.

EXAMPLE 10

Acute toxicity test

The following acute toxicity test was conducted on mice:

Animal: Five-week old ddY male mice (wt: 21–27 g) in groups of 6.

Method: The mice were starved overnight and the compound prepared in Example 6 was administered perorally in an amount of 0.1 ml/10 g body weight after it was suspended in 0.5% carboxymethyl cellulose sodium salt (CMC-Na). As a control, 0.5% CMC-Na solution was administered.

The results are shown in Table 2.

TABLE 2

| Compound | Dosage (mg/kg) | Mortality |
| --- | --- | --- |
| 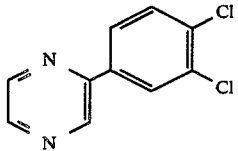 (Example 6) | 500<br>1000<br>2000<br>5000 | 0/6<br>0/6<br>0/6<br>0/6 |
| Control | — | 0/6 |

As the table shows, none of the animals treated with the compound of Example 6 died at the dosage levels used. The compound did not show any delayed toxicity, either. No apparent changes were observed in the general condition of the mice.

The compound of the present invention are highly effective in inhibiting the formation of thrombi induced by ADP or collagen and, hence, have potential for use as drugs which are effective against a variety of thromotic diseases such as myocardial infarction and cerebral thrombosis. In addition, as demonstrated below, the compounds have low levels of toxicity and can be used as safe pharmaceuticals.

I claim:

1. A phenylpyrazine of the formula:

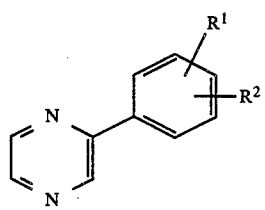

where $R^1$ is a hydrogen atom, a halogen atom, a lower alkoxy group or a hydroxyl group; and $R^2$ is a halogen atom or a hydroxyl group.

2. A compound according to claim 1 wherein $R^1$ is a hydrogen atom or a halogen atom; and $R^2$ is a halogen atom.

3. A compound according to claim 1 where $R^1$ is an alkoxy group having 1 to 4 carbon atoms.

4. A pharmaceutical composition comprising:
   a thrombolytically effective amount of phenylpyrazine represented by the formula,

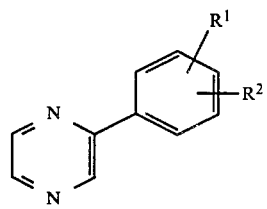

where $R^1$ is a hydrogen atom, a halogen atom, a lower alkoxy group or a hydroxyl group and $R^2$ is a halogen atom or a hydroxyl group; and
   a pharmaceutically acceptable carrier.

5. A method of preventing the formation of thrombi in mammals comprising the step of administering a pharmaceutical composition comprising:
   a thrombolytically effective amount of phenylpyrazine represented by the formula,

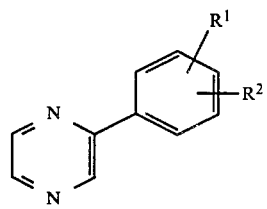

where $R^1$ is a hydrogen atom, a halogen atom, a lower alkyl group, a lower alkoxy group or a hydroxyl group and $R^2$ is a halogen atom, a lower alkyl group, a lower alkoxy group or a hydroxyl group; and
   a pharmaceutically acceptable carrier.

6. A method of treating thrombisis in mammals comprising the step of administering a pharmaceutical composition comprising:
   a thrombolytically effective amount of phenylpyrazine represented by the formula,

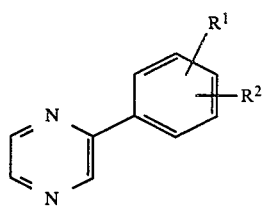

where $R^1$ is a hydrogen atom, a halogen atom, a lower alkyl group, a lower alkoxy group or a hydroxyl group; and $R^2$ is a halogen atom, a lower alkyl group, a lower alkoxy group or a hydroxyl group; and
   a pharmaceutically acceptable carrier.

* * * * *

UNITED STATES PATENT AND TRADEMARK OFFICE
CERTIFICATE OF CORRECTION

PATENT NO. : 4,755,514

DATED : July 5, 1988

INVENTOR(S) : OHTA

It is certified that error appears in the above-identified patent and that said Letters Patent is hereby corrected as shown below:

<u>IN THE SPECIFICATION:</u>

Column 6, line 10, change "30 mg/kg" to --300 mg/kg--;

line 12, before "collagen" insert --30 mg/kg of--.

Signed and Sealed this

Tenth Day of July, 1990

Attest:

HARRY F. MANBECK, JR.

*Attesting Officer*  *Commissioner of Patents and Trademarks*